United States Patent
Rajtar et al.

(10) Patent No.: US 7,071,154 B2
(45) Date of Patent: Jul. 4, 2006

(54) AZEOTROPE-LIKE COMPOSITIONS AND THEIR USE

(75) Inventors: Paul E. Rajtar, Hugo, MN (US); John G. Owens, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 221 days.

(21) Appl. No.: 10/739,231

(22) Filed: Dec. 18, 2003

(65) Prior Publication Data

US 2005/0137113 A1 Jun. 23, 2005

(51) Int. Cl.
*C11D 7/50* (2006.01)

(52) U.S. Cl. .................. 510/411; 510/407; 510/408; 510/412

(58) Field of Classification Search ............... None
See application file for complete search history.

(56) References Cited

U.S. PATENT DOCUMENTS

| 5,814,595 | A | 9/1998 | Flynn et al. |
| 5,827,812 | A | 10/1998 | Flynn et al. |
| 5,925,611 | A | 7/1999 | Flynn et al. |
| 6,030,934 | A | 2/2000 | Owens et al. |
| 6,043,201 | A | 3/2000 | Milbrath et al. |
| 6,291,417 | B1 | 9/2001 | Flynn et al. |
| 6,372,700 | B1 | 4/2002 | Zazerra et al. |
| 6,423,673 | B1 | 7/2002 | Owens et al. |
| 6,492,309 | B1 | 12/2002 | Behr et al. |
| 6,506,459 | B1* | 1/2003 | Flynn et al. ............ 427/498 |
| 2001/0044404 | A1* | 11/2001 | Flynn et al. ............ 510/412 |
| 2002/0094944 | A1* | 7/2002 | Flynn et al. ............ 510/412 |
| 2002/0119901 | A1* | 8/2002 | Flynn et al. ............ 510/407 |
| 2002/0124326 | A1* | 9/2002 | Flynn et al. ............ 8/142 |
| 2002/0169098 | A1* | 11/2002 | Flynn et al. ............ 510/412 |

FOREIGN PATENT DOCUMENTS

WO    WO 97/22683    6/1997

OTHER PUBLICATIONS

B. N. Ellis in *Cleaning and Contamination of Electronics Components and Assemblies*, Electrochemical Publications Limited, Ayr, Scotland, pp. 182-194 (1986).
U.S. Appl. No. 10/673,821, filed Sep. 29, 2003, Azeotrope-Like Compositions Containing Hexafluoropropylene Dimer and Use Thereof.

* cited by examiner

*Primary Examiner*—Gregory Webb
(74) *Attorney, Agent, or Firm*—Thomas M. Spielbauer

(57) ABSTRACT

Azeotrope-like compositions comprising $C_2F_5CF(OCH_3)CF(CF_3)_2$ (1,1,1,2,2,3,4,5,5,5-decafluoro-3-methoxy-4-trifluoromethyl-pentane) and an organic solvent, and uses thereof, are described.

14 Claims, 3 Drawing Sheets

AZEOTROPE-LIKE COMPOSITIONS AND THEIR USE

FIELD

This invention relates to azeotrope and azeotrope-like compositions containing 1,1,1,2,2,3,4,5,5,5-decafluoro-3-methoxy-4-trifluoromethyl-pentane, and methods of using azeotropes and azeotrope-like compositions to clean substrates, deposit coatings (e.g., cosmetics), transfer thermal energy, and lubricate working operations.

BACKGROUND

Chlorofluorocarbons (CFCs), hydrochlorofluorocarbons (HCFCs), and hydrochlorocarbons (HCCs, e.g., 1,1,1-trichloroethane and carbon tetrachloride) have been used in a wide variety of solvent applications such as drying, cleaning (e.g., the removal of flux residues from printed circuit boards), and vapor degreasing. These materials have also been used in refrigeration and heat-transfer processes. However, the photolytic and homolytic reactivity at the chlorine-containing carbon sites has been shown to contribute to depletion of the earth's ozone layer. Additionally, the long atmospheric lifetime of CFCs has been linked to global warming. As a result, there has been a world-wide movement for over a decade to replace CFCs. (See "Montreal Protocol on Substances That Deplete the Ozone Layer," Copenhagen Amendments, United Nations Environment Program, 1992).

The characteristics sought in replacements, in addition to low ozone depletion potential, typically have included boiling point ranges suitable for a variety of solvent cleaning applications, low flammability, and low toxicity. For some applications, solvent replacements should also have the ability to dissolve both hydrocarbon-based and fluorocarbon-based soils. In some embodiments, solvent replacements also have low toxicity, have no flash points (as measured by ASTM D3278-98 e-1, "Flash Point of Liquids by Small Scale Closed-Cup Apparatus" otherwise known as SETAFLASH), have acceptable stability, have short atmospheric lifetimes, and have low global warming potentials.

Hydrofluoroethers (HFEs) have gained interest as replacements for CFCs and HCFCs. Generally, HFEs are chemically stable, have low toxicity, are non-flammable, and are non-ozone depleting. Mixtures of HFEs with other organic solvents tend to be better solvents and dispersants for hydrocarbons than HFEs alone.

Many azeotropes possess properties that make them useful solvents. For example, azeotropes have a constant boiling point that avoids boiling temperature drift during processing and use. In addition, when an azeotrope is used as a solvent, the properties of the solvent remain constant because the composition of the solvent does not change during boiling or reflux. Azeotropes that are used as solvents also can be recovered conveniently by distillation.

In some embodiments, it is desirable to provide azeotropes or azeotrope-like compositions that have good solvent strength. In another aspect, in some embodiments, it is desirable to provide azeotropes or azeotrope-like compositions that have low flammability. In yet another aspect, in some embodiments, it is desirable to provide azeotropes or azeotrope-like compositions that are non-ozone depleting, and/or have a relatively short atmospheric lifetime so that they do not significantly contribute to global warming (i.e., azeotropes or azeotrope-like compositions that have low global warming potential).

SUMMARY

Briefly, in one aspect, the present invention provides azeotrope-like compositions comprising a blend of $C_2F_5CF(OCH_3)CF(CF_3)_2$ and an organic solvent. The organic solvents of the present invention include 1-bromopropane, hexamethyldisilazane, isobutyl acetate, methylisobutyl ketone, trans-1,2-dichloroethylene, and trifluoromethylbenzene. In some embodiments, the azeotrope-like compositions of the present invention further comprise a lubricious additive, ozone, and/or hydrofluoric acid.

In another aspect, the present invention provides a coating composition comprising an azeotrope-like composition at least one coating material soluble or dispersible in the azeotrope-like composition.

In yet another aspect, the present invention provides a process for depositing a coating on a substrate surface comprising the step of applying a coating composition comprising an azeotrope-like composition to at least a portion of at least one surface of the substrate, wherein the at least one coating material is soluble or dispersible in the azeotrope-like composition.

In yet another aspect, the present invention provides a process for metal, cermet, or composite wherein said process is lubricated using a working fluid comprising an azeotrope-like composition of the present invention.

In yet another aspect, the present invention provides a process for removing contaminants from the surface of a substrate comprising the steps of contacting the substrate with one or more of the azeotrope-like compositions according to the present invention until the contaminants are dissolved, dispersed, or displaced in or by the azeotrope-like composition, and removing the azeotrope-like composition containing the dissolved, dispersed or displaced contaminants from the surface of the substrate.

In yet another aspect, the present invention provides a process for heat transfer wherein one or more of the azeotrope-like compositions according to the present invention is used as a heat-transfer fluid.

The above summary of the present invention is not intended to describe each embodiment of the present invention. The details of one or more embodiments of the invention are also set forth in the description below. Other features, objects, and advantages of the invention will be apparent from the description and from the claims.

DETAILED DESCRIPTION

Figure 1:
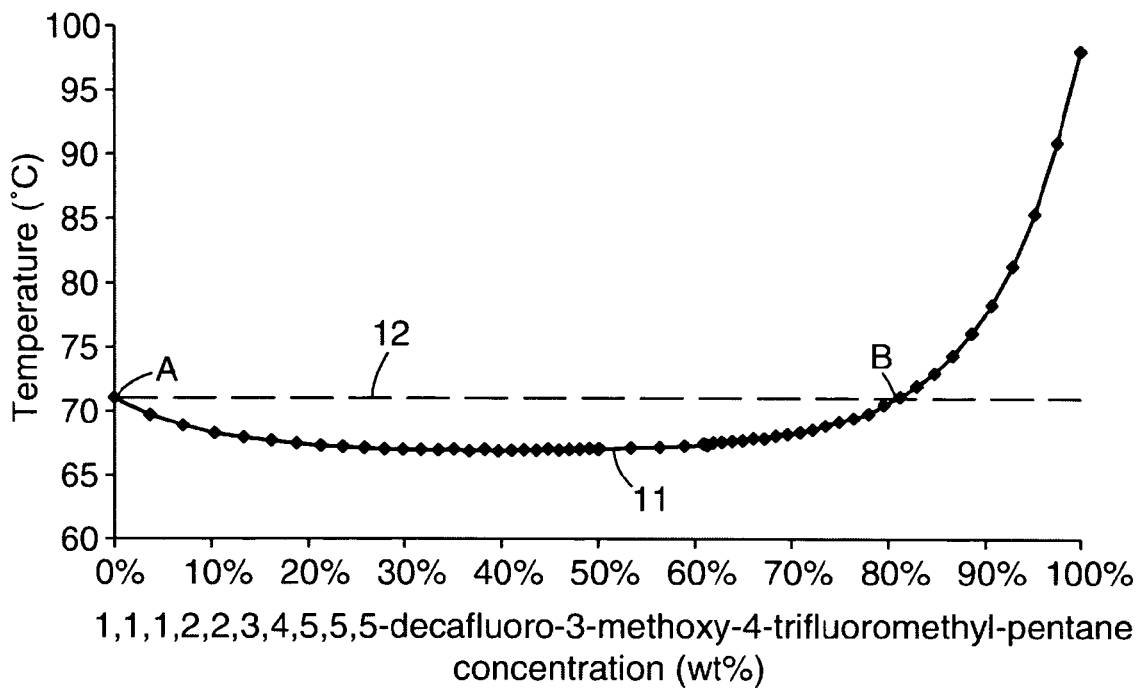
FIG. 1 is a graph of the boiling point versus the weight percent of $C_2F_5CF(OCH_3)CF(CF_3)_2$ in solution with 1-bromopropane. Points A and B indicate the endpoints for the azeotrope-like composition.

An azeotropic composition or azeotrope comprises a mixture of two or more substances that behaves like a single substance in that the vapor produced by partial evaporation of the liquid at its boiling point has the same composition as the liquid. Azeotropic compositions are constant boiling point mixtures that exhibit either a maximum or a minimum boiling point as compared with other compositions of the same substances.

A mixture of substances that forms an azeotrope exhibits strong thermodynamic non-ideality. A thermodynamically ideal or slightly non-ideal mixture has a boiling point between the boiling points of the two components. Azeotrope-like compositions of the present invention exhibit strong thermodynamic non-ideality in that the azeotrope-like compositions of the present invention boil at temperatures that are below the boiling point of the minimum boiling point component. The range of azeotrope-like compositions for a particular mixture of substances includes the corresponding azeotrope. See FIGS. 1–6.

The azeotrope-like compositions of the present invention comprise an organic solvent and 1,1,1,2,2,3,4,5,5,5-decafluoro-3-methoxy-4-trifluoromethyl-pentane, a hydrofluoroether (HFE) described by the formula $C_2F_5CF(OCH_3)CF(CF_3)_2$. The concentration of the organic solvent and the HFE in a particular azeotrope-like composition may vary substantially from the corresponding azeotropic composition, and the magnitude of this permissible variation depends upon the organic solvent. In some embodiments, the azeotropic-like composition comprises essentially the same concentrations of the organic solvent and the HFE as comprise the azeotrope formed between them at ambient pressure. In some embodiments, the azeotrope-like compositions exhibit no significant change in the solvent power of the composition over time.

Typically, azeotropes retain many of the properties of the individual component solvents, which can enhance performance and usefulness over the individual components because of the combined properties.

The azeotrope-like compositions of this invention may also contain, in addition to the organic solvent and the HFE, other compounds that do not interfere in the formation of the azeotrope. Typically, the other compounds will be present in small amounts. For example, in some embodiments, co-solvents or surfactants may be present in the azeotrope-like compositions of the present invention to, for example, improve the dispersibility or the solubility of materials, such as water, soils, or coating materials (e.g., perfluoropolyether lubricants and fluoropolymers), in an azeotrope and azeotrope-like compositions. In some embodiments, small amounts of lubricious additives may be present to, for example, enhance the lubricating properties of an azeotrope and azeotrope-like compositions.

The organic solvents of the present invention include 1-bromopropane, hexamethyldisilazane, isobutyl acetate, methylisobutyl ketone, trans-1,2-dichloroethylene, and trifluoromethylbenzene (obtained under the trade designation OXSOL 2000 from MANA, located in New York, N.Y.).

The hydrofluoroether (HFE) of the present invention is 1,1,1,2,2,3,4,5,5,5-decafluoro-3-methoxy-4-trifluoromethyl-pentane, as described by the formula $C_2F_5CF(OCH_3)CF(CF_3)_2$.

Azeotrope-like compositions of the present invention comprise blends of 1,1,1,2,2,3,4,5,5,5-decafluoro-3-methoxy-4-trifluoromethyl-pentane (HFE) and an organic solvent, wherein the blends include (i) blends consisting essentially of about 1 to about 81 weight percent of $C_2F_5CF(OCH_3)CF(CF_3)_2$ and about 99 to about 19 weight percent of 1-bromopropane that boil below about 71.0° C. at about 101 kilopascals (kPa) (760 torr);

(ii) blends consisting essentially of about 23 to about 99 weight percent of $C_2F_5CF(OCH_3)CF(CF_3)_2$ and about 77 to about 1 weight percent of trifluoromethylbenzene that boil below about 98.0° C. at about 101 kPa (760 torr);

(iii) blends consisting essentially of about 65 to about 99 weight percent of $C_2F_5CF(OCH_3)CF(CF_3)_2$ and about 35 to about 1 weight percent of hexamethyldisilazane that boil below about 97.9° C. at about 101 kPa (760 torr);

(iv) blends consisting essentially of about 68 to about 99 weight percent of $C_2F_5CF(OCH_3)CF(CF_3)_2$ and about 32 to about 1 weight percent of isobutyl acetate that boil below about 98.1° C. at about 101 kPa (760 torr);

(v) blends consisting essentially of about 70 to about 99 weight percent of $C_2F_5CF(OCH_3)CF(CF_3)_2$ and about 30 to about 1 weight percent of methylisobutyl ketone that boil below about 98.0° C. at about 101 kPa (760 torr); and (vi) blends consisting essentially of about 1 to about 59 weight percent of $C_2F_5CF(OCH_3)CF(CF_3)_2$ and about 99 to about 41 weight percent of trans-1,2-dichloroethylene that boil below about 47.7° C. at about 101 kPa (760 torr).

As is known in the art, as the ambient pressure increases, the boiling point of a liquid increases, and similarly, as the ambient pressure decreases, the boiling point of a liquid decreases.

In some embodiments, the azeotrope-like compositions of the present invention have a boiling point of less than 75% of the boiling point depression from the lowest boiling point component to the minimum boiling point of the azeotrope-like composition. That is, if the boiling point of the lowest boiling point component is X, and the boiling point of the minimum boiling point of the azeotrope-like composition is Y, then the boiling point of these azeotrope-like compositions would be less than X−0.25 (X−Y).

These azeotrope-like compositions of the present invention comprise blends of 1,1,1,2,2,3,4,5,5,5-decafluoro-3-methoxy-4-trifluoromethyl-pentane (HFE) and an organic solvent, wherein the blends include (i) blends consisting essentially of about 3 to about 78 weight percent of $C_2F_5CF(OCH_3)CF(CF_3)_2$ and about 97 to about 22 weight percent of 1-bromopropane that boil below about 70.0° C. at about 101 kPa (760 torr);

(ii) blends consisting essentially of about 30 to about 97 weight percent of $C_2F_5CF(OCH_3)CF(CF_3)_2$ and about 70 to about 3 weight percent of trifluoromethylbenzene that boil below about 97.0° C. at about 101 kPa (760 torr);

(iii) blends consisting essentially of about 68 to about 99 weight percent of $C_2F_5CF(OCH_3)CF(CF_3)_2$ and about 32 to about 1 weight percent of hexamethyldisilazane that boil below about 97.4° C. at about 101 kPa (760 torr);

(iv) blends consisting essentially of about 71 to about 99 weight percent of $C_2F_5CF(OCH_3)CF(CF_3)_2$ and about 29 to about 1 weight percent of isobutyl acetate that boil below about 97.8° C. at about 101 kPa (760 torr);

(v) blends consisting essentially of about 73 to about 99 weight percent of $C_2F_5CF(OCH_3)CF(CF_3)_2$ and about 27 to about 1 weight percent of methylisobutyl ketone that boil below about 97.6° C. at about 101 kPa (760 torr); and (vi) blends consisting essentially of about 2 to about 55 weight percent of $C_2F_5CF(OCH_3)CF(CF_3)_2$ and about 98 to about 45 weight percent of trans-1,2-dichloroethylene that boil below about 47.6° C. at about 101 kPa (760 torr).

In some embodiments, the azeotrope-like compositions of the present invention have a boiling point of less than 50% of the boiling point depression from the lowest boiling point component to the minimum boiling point of the azeotrope-like composition. That is, if the boiling point of the lowest boiling point component is X, and the boiling point of the minimum boiling point of the azeotrope-like composition is Y, then the boiling point of these azeotrope-like compositions would be less than X−0.5 (X−Y).

These azeotrope-like compositions of the present invention comprise blends of 1,1,1,2,2,3,4,5,5,5-decafluoro-3-methoxy-4-trifluoromethyl-pentane (HFE) and an organic solvent, wherein the blends include (i) blends consisting essentially of about 7 to about 74 weight percent of $C_2F_5CF(OCH_3)CF(CF_3)_2$ and about 93 to about 26 weight percent of 1-bromopropane that boil below about 68.9° C. at about 101 kPa (760 torr);

(ii) blends consisting essentially of about 39 to about 94 weight percent of $C_2F_5CF(OCH_3)CF(CF_3)_2$ and about 61 to about 6 weight percent of trifluoromethylbenzene that boil below about 96.1° C. at about 101 kPa (760 torr);

(iii) blends consisting essentially of about 73 to about 98 weight percent of $C_2F_5CF(OCH_3)CF(CF_3)_2$ and about 27 to about 2 weight percent of hexamethyldisilazane that boil below about 96.9° C. at about 101 kPa (760 torr);

(iv) blends consisting essentially of about 76 to about 97 weight percent of $C_2F_5CF(OCH_3)CF(CF_3)_2$ and about 24 to about 3 weight percent of isobutyl acetate that boil below about 97.5° C. at about 101 kPa (760 torr);

(v) blends consisting essentially of about 77 to about 98 weight percent of $C_2F_5CF(OCH_3)CF(CF_3)_2$ and about 23 to about 2 weight percent of methylisobutyl ketone that boil below about 97.2° C. at about 101 kPa (760 torr); and (vi) blends consisting essentially of about 5 to about 50 weight percent of $C_2F_5CF(OCH_3)CF(CF_3)_2$ and about 95 to about 50 weight percent of trans-1,2-dichloroethylene that boil below about 47.4° C. at about 101 kPa (760 torr).

The azeotrope compositions of the present invention comprise blends of 1,1,1,2,2,3,4,5,5,5-decafluoro-3-methoxy-4-trifluoromethyl-pentane (HFE) and an organic solvent, wherein the blends include (i) blends consisting essentially of about 55.4 weight percent of $C_2F_5CF(OCH_3)CF(CF_3)_2$ and about 44.6 weight percent of 1-bromopropane that boil at about 65.4° C. at about 97.8 kPa (734 torr);

(ii) blends consisting essentially of about 71.3 weight percent of $C_2F_5CF(OCH_3)CF(CF_3)_2$ and about 28.7 weight percent of trifluoromethylbenzene that boil at about 92.3° C. at about 97.7 kPa (733 torr);

(iii) blends consisting essentially of about 90.0 weight percent of $C_2F_5CF(OCH_3)CF(CF_3)_2$ and about 10.0 weight percent of hexamethyldisilazane that boil at about 93.6° C. at about 97.3 kPa (730 torr);

(iv) blends consisting essentially of about 91.8 weight percent of $C_2F_5CF(OCH_3)CF(CF_3)_2$ and about 8.2 weight percent of isobutyl acetate that boil at about 94.5° C. at about 96.8 kPa (726 torr);

(v) blends consisting essentially of about 90.5 weight percent of $C_2F_5CF(OCH_3)CF(CF_3)_2$ and about 9.5 weight percent of methylisobutyl ketone that boil at about 94.0° C. at about 96.6 kPa (725 torr); and (vi) blends consisting essentially of about 22.7 weight percent of $C_2F_5CF(OCH_3)CF(CF_3)_2$ and about 77.3 weight percent of trans-1,2-dichloroethylene that boil at about 45.7° C. at about 98.6 kPa (740 torr).

In some embodiments, the azeotrope-like compositions of the present invention are homogeneous; i.e., they form a single phase under ambient conditions (i.e., at room temperature and atmospheric pressure).

The azeotrope-like compositions of the present invention can be prepared by mixing the desired amounts of $C_2F_5CF(OCH_3)CF(CF_3)_2$, the organic solvent, and any other minor components (e.g., surfactants or lubricious additives) together using conventional mixing means.

In some embodiments, the azeotrope-like compositions of the present invention may be used in cleaning processes, in heat-transfer processes, as refrigerants, as a working fluid, as a coating liquid (e.g., a cosmetic), and the like.

The cleaning process of the present invention can be carried out by contacting a contaminated substrate with one of the azeotrope-like compositions of this invention until the contaminants on the substrate are substantially dissolved, dispersed, or displaced in or by the azeotrope-like composition, and then removing (for example, by rinsing the substrate with fresh, uncontaminated azeotrope-like composition or by removing a substrate immersed in an azeotrope-like composition from the bath and permitting the contaminated azeotrope-like composition to flow off of the substrate) the azeotrope-like composition containing the dissolved, dispersed, or displaced contaminant from the substrate. The azeotrope-like composition can be used in either the vapor or the liquid state (or both), and any of the known techniques for "contacting" a substrate can be used. For example, the liquid azeotrope-like composition can be sprayed or brushed onto the substrate, the vaporous azeotrope-like composition can be blown across the substrate, or the substrate can be immersed in either a vaporous or a liquid azeotrope-like composition. In some embodiments, elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182–94 (1986).

In some embodiments, exemplary processes of the invention can be used to clean organic and/or inorganic substrates. Representative examples of substrates include metals; ceramics; glass; silicon wafers; polymers such as, for example, polycarbonate, polystyrene, and acrylonitrile-butadiene-styrene copolymer; natural fibers (and fabrics derived therefrom) such as, for example, cotton, silk, linen, wool, ramie, fur, leather, and suede; synthetic fibers (and fabrics derived therefrom) such as, for example, polyester, rayon, acrylics, nylon, polyolefin, acetates, triacetates, and blends thereof; fabrics comprising a blend of natural and synthetic fibers; and composites of the foregoing materials. In some embodiments, the process of the present invention is especially useful in the precision cleaning of electronic components (e.g., circuit boards); optical or magnetic media; and medical devices and medical articles such as, for example, syringes, surgical equipment, implantable devices, and prosthesis. In some embodiments, the exemplary processes of the invention can be used to remove nail polish.

In some embodiments, exemplary cleaning processes of the present invention can be used to dissolve or remove most contaminants from the surface of a substrate. For example, materials such as light hydrocarbon contaminants; higher molecular weight hydrocarbon contaminants such as mineral oils, greases, cutting and stamping oils and waxes; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; and other contaminants encountered in precision, electronic, metal, and medical device cleaning can be removed. In some embodiments, the process of the present invention is particularly useful for the removal of hydrocarbon contaminants (especially, light hydrocarbon oils), fluorocarbon contaminants, and particulates.

In some embodiments, the azeotrope-like compositions of the present invention are also useful for extraction. Here, cleaning involves removing contaminants (e.g., fats, waxes, oils, or other solvents) by dissolution or displacement of these materials from substances (e.g., naturally occurring materials, foods, cosmetics, pharmaceuticals).

In some embodiments, exemplary azeotrope-like compositions of the present invention can also be used in coating deposition applications, where the azeotrope-like composition functions as a carrier for a coating material to enable deposition of the material on the surface of a substrate. The invention thus also provides a coating composition comprising the azeotrope-like composition and a process for depositing a coating on a substrate surface using the azeotrope-like composition. The process comprises the step of applying to at least a portion of at least one surface of a substrate a coating of a liquid coating composition comprising (a) an azeotrope-like composition; and (b) at least one coating material that is soluble or dispersible in the azeotrope-like composition. The coating composition can further comprise one or more additives (e.g., surfactants, coloring agents, stabilizers, anti-oxidants, flame retardants, and the like). Preferably, the process further comprises the step of removing the azeotrope-like composition from the deposited coating by, e.g., allowing evaporation (which can be aided by the application of, e.g., heat or vacuum).

The coating materials that can be deposited by the process include pigments, silicone lubricious additives, stabilizers, adhesives, anti-oxidants, dyes, polymers, pharmaceuticals, cosmetics, release agents, inorganic oxides, and the like, and combinations thereof. Preferred materials include perfluoropolyethers, hydrocarbons, and silicone lubricious additives; amorphous copolymers of tetrafluoroethylene; polytetrafluoroethylene; and combinations thereof. Representative examples of materials suitable for use in the process include titanium dioxide, iron oxides, magnesium oxide, perfluoropolyethers, polysiloxanes, stearic acid, acrylic adhesives, polytetrafluoroethylene, amorphous copolymers of tetrafluoroethylene, and combinations thereof. Any of the substrates described above (for cleaning applications) can be coated via the process of the invention. The process can be particularly useful for coating magnetic hard disks or electrical connectors with perfluoropolyether lubricants or medical devices with silicone lubricious additives.

In some embodiments, the substrate may be skin. In some embodiments, the liquid coating composition may be used as, for example, a cosmetic, a lotion, or a nail polish.

To form a coating composition, the components of the composition (i.e., the azeotrope-like composition, the coating material(s), and any additive(s) utilized) can be combined by any conventional mixing technique used for dissolving, dispersing, or emulsifying coating materials, e.g., by mechanical agitation, ultrasonic agitation, manual agitation, and the like. The azeotrope-like composition and the coating material(s) can be combined in any ratio depending upon the desired thickness of the coating. In some embodiments, the coating material(s) constitute from about 0.1 to about 10 weight percent of the coating composition.

Exemplary deposition processes of the invention can be carried out by applying the coating composition to a substrate by any conventional technique. For example, the composition can be brushed or sprayed (e.g., as an aerosol) onto the substrate, or the substrate can be spin-coated. In some embodiments, the substrate is coated by immersion in the composition. Immersion can be carried out at any suitable temperature and can be maintained for any convenient length of time. If the substrate is a tubing, such as a catheter, and it is desired to ensure that the composition coats the lumen wall, it may be advantageous to draw the composition into the lumen by the application of reduced pressure.

In some embodiments, after a coating is applied to a substrate, the azeotrope-like composition can be removed from the deposited coating by evaporation. In some embodiments, the rate of evaporation can be accelerated by application of reduced pressure or mild heat. The coating can be of any convenient thickness. Generally, the thickness will be determined by, for example, such factors as the viscosity of the coating material, the temperature at which the coating is applied, and the rate of withdrawal (if immersion is utilized).

In some embodiments, the azeotrope-like compositions of the present invention can be used as heat-transfer fluids in heat-transfer processes where the heat-transfer fluids can transfer thermal energy (i.e., heat) either in a direct or indirect manner. Direct heat transfer (sometimes called "direct contact heat transfer") refers to a heat-transfer process wherein a heat-transfer fluid conducts heat directly (i.e., through conduction and/or convection) to and/or from a heat sink or source to a fluid by directly contacting the fluid with the heat sink or source. Examples of direct heat transfer include the immersion cooling of electrical components and the cooling of an internal combustion engine.

Indirect heat transfer refers to a heat-transfer process wherein a heat-transfer fluid conducts heat to and/or from a heat sink or source without directly contacting the fluid with the heat sink or source. Examples of indirect heat transfer include refrigeration, air conditioning and/or heating (e.g., using heat pumps) processes, such as are used in buildings, vehicles, and stationary machinery. In one embodiment, the present invention provides a process for transferring heat comprising employing an azeotropic composition of the present invention as a secondary loop refrigerant. In this embodiment, the secondary loop refrigerant (i.e., a wide temperature range liquid fluid) provides a means for transferring heat between the heat source (i.e., object to be cooled) and the primary loop refrigerant (i.e., a low temperature-boiling fluid which accepts heat by expanding to a gas and rejects heat by being condensed to a liquid, typically by using a compressor). Examples of equipment in which the azeotropic composition of this invention may be useful include, but are not limited to, centrifugal chillers, household refrigerator/freezers, automotive air conditioners, refrigerated transport vehicles, heat pumps, supermarket food coolers and display cases, and cold storage warehouses.

In indirect heat-transfer processes, lubricious additives for heat transfer can be incorporated in the heat-transfer fluid where moving parts (e.g., pumps and valves) are involved to ensure that the moving parts continue to work over long periods of time. Generally, these lubricious additives should possess good thermal and hydrolytic stability and should exhibit at least partial solubility in the heat-transfer fluid. Examples of suitable lubricious additives include mineral oils, fatty esters, highly halogenated oils such as chlorotrifluoroethylene-containing polymers, and synthetic lubricious additives such as alkylene oxide polymers.

In some embodiments, the azeotrope-like compositions of the present invention can be used to formulate working fluids or lubricants that comprise the azeotrope-like compositions of the present invention and at least one fully volatile lubricious additive. A lubricious additive for working operations is defined herein as an additive that modifies the coefficient of friction between a workpiece and tooling. In some embodiments, an azeotrope-like composition of the present invention with the lubricious additive form the working fluid for the working operation.

Exemplary substrates in working operations include metal, cermet, and composite workpieces. Exemplary metals include refractory metals (e.g., tantalum, niobium, molybdenum, vanadium, tungsten, hafnium, rhenium, and titanium); precious metals (e.g., silver, gold, and platinum); high temperature metals (e.g., nickel, titanium alloys, and nickel chromes); other metals including, for example, magnesium, copper, aluminum, steel (e.g., stainless steels); alloys (e.g., brass, and bronze); and any combinations thereof.

Typically, working fluids lubricate machining surfaces, resulting in a smooth and substantially residue-free machined workpiece surface. In some embodiments, exemplary working fluids of the present invention used in these operations also cool the machining environment (i.e., the surface interface between a workpiece and a machining tool) by, for example, removing heat and/or particulate matter therefrom.

Cermets are defined as semisynthetic-products consisting of a mixture of ceramic and metallic components having physical properties not found solely in either one alone. Examples include, but are not limited to, metal carbides, oxides, and silicides. See Hawley's Condensed Chemical Dictionary, 12$^{th}$ Edition, Van Nostrand Reinhold Company, 1993.

Composites are described herein as laminates of high temperature fibers in a polymer matrix, for example, a glass or carbon fiber in an epoxy resin.

In some embodiments, a working fluid of the present invention is formulated so that the cutting and forming processes are lubricated to reduce friction, heat build-up in the tool or workpiece, and/or prevent material transfer from the workpiece to the tool. In some embodiments, a working fluid of the present invention filly wets the working tooling. In some embodiments, the azeotrope-like composition included in the working liquid evaporates from the working tool and workpiece. In some embodiments, the lubricious additive is present as a thin film that reduces friction and heat build-up on the surfaces of the tool and workpiece, and/or prevents material transfer from the workpiece to the tooling. Generally, the lubricious additive is selected such that it is sufficiently high in boiling point to lubricate the working process without evaporating prematurely and still low enough in boiling point to fully evaporate from the working process so that little or no residue remains. Examples of lubricious additives for working operations include, but are not limited to, esters of $C_8$ to $C_{14}$ fatty acids, alkylene glycol ethers, hydrocarbon distillates, and esters of lactic acid.

In each of the described uses, the azeotrope-like or azeotrope composition can be used per se, or a blend of azeotrope-like compositions may be used, provided the blend is azeotrope-like. Similarly, minor amounts of co-solvents can be added to the azeotrope-like compositions, provided the addition does not disrupt the azeotropic behavior, or that the addition produces a ternary azeotrope. Useful co-solvents may include, for example, CFCs, HCFCs, hydrofluorocarbons (HFCs), hydrocarbons, hydrochlorocarbons (HCCs), or water. Representative examples of suitable co-solvents include carbon dioxide; 1,1-difluoroethane; 1,1-dichloro-1-fluoroethane; 1,1-dichloro-2,2,2-trifluoroethane; 1-hydropentadecafluoroheptane; 1,1,1,2-tetrafluoroethane; chlorodifluoromethane; 1,1,1,3,3-pentafluoropropane; trans-1,2-dichloroethene; 1-chloro-1,1-difluoroethane; 2-chloropropane; chlorofluorocarbons (e.g., fluorotrichloromethane); water; saturated perfluorochemicals (e.g., perfluoropentane, perfluorohexane, and perfluoro(N-methylmorpholine)); and combinations thereof. In some embodiments, the azeotrope-like composition may further comprise ozone and/or hydrofluoric acid (HF).

EXAMPLES

The preparation, identification, and testing of the azeotrope-like compositions of this invention are further described in the following examples. The particular materials and amounts thereof recited in these examples, as well as other conditions and details, should not be construed to unduly limit this invention. In these examples, all percentages, proportions and ratios are by weight unless otherwise indicated.

1,1,1,2,2,3,4,5,5,5-decafluoro-3-methoxy-4-trifluoromethyl-pentane ($C_2F_5CF(OCH_3)CF(CF_3)_2$) was prepared according to methods described in U.S. Pat. No. 5,925,611. The material used in the following examples was 99.96% pure as determined by NMR analysis.

Examples 1–6

Various mixtures of $C_2F_5CF(OCH_3)CF(CF_3)_2$ and organic solvent were distilled at ambient pressure (725 to 740 torr) to identify whether they formed binary azeotropes, and if so, the composition (percent by weight) and boiling point (b.p ° C.) of the azeotrope, using the following procedure. The mixtures were prepared and distilled at ambient lab pressure (725 to 740 torr) in a concentric tube distillation column (Model 933 obtained from Ace Glass, Vinland, N.J.). In each case, the distillation was allowed to equilibrate at total reflux for at least 60 minutes. For each distillation, six successive distillate samples, each approximately 5 percent by volume of the total liquid charge, were taken while operating the column at a liquid reflux ratio of 20 to 1. The compositions of the distillate samples were then analyzed using an HP-5890 Series II Plus Gas Chromatograph with an RTX-200 capillary column (obtained from Restek Corporation, Bellefonte, Pa.) and Nukol capillary column (obtained from Supelco, Bellefonte, Pa.) or a Quadrex 007 Series Methyl Silicone capillary column (obtained from Quadrex Corporation, New Haven, Conn.) and a thermal conductivity detector. The boiling point of each distillate was measured using a thermocouple. Following this test procedure, azeotropes of $C_2F_5CF(OCH_3)CF(CF_3)_2$ were identified with 1-bromopropane (obtained from Aldrich, St. Louis, Mo.); trifluoromethyl benzene (obtained from MANA, New York, N.Y.); hexamethyldisilazane (obtained from Aldrich, St. Louis, Mo.); isobutyl acetate (obtained from Aldrich); methylisobutyl ketone (obtained from Aldrich); and trans-1,2-dichloroethylene (obtained from PPG Industries, Pittsburgh, Pa.).

In Table 1 shown below, the compositions (percent by weight) and boiling points at the indicated pressure) of the six azeotropes are presented as Examples 1–6.

TABLE 1

| Example | Composition | Boiling Point (° C.) | Pressure (kPa) | Pressure (torr) |
|---|---|---|---|---|
| 1 | 44.6% 1-bromopropane<br>55.4% $C_2F_5CF(OCH_3)CF(CF_3)_2$ | 65.4 | 97.8 | 734 |
| 2 | 28.7% trifluoromethyl benzene<br>71.3% $C_2F_5CF(OCH_3)CF(CF_3)_2$ | 92.3 | 97.7 | 733 |
| 3 | 10.0% hexamethyldisilazane<br>90.0% $C_2F_5CF(OCH_3)CF(CF_3)_2$ | 93.6 | 97.3 | 730 |
| 4 | 8.2% isobutyl acetate<br>91.8% $C_2F_5CF(OCH_3)CF(CF_3)_2$ | 94.5 | 96.8 | 726 |
| 5 | 9.5% methylisobutyl ketone<br>90.5% $C_2F_5CF(OCH_3)CF(CF_3)_2$ | 94.0 | 96.6 | 725 |
| 6 | 77.3% trans-1,2-dichloroethylene<br>22.7% $C_2F_5CF(OCH_3)CF(CF_3)_2$ | 45.7 | 98.6 | 740 |

Examples 7–12

Percentage ranges for azeotrope-like compositions of the invention were identified by determining boiling points of test mixtures of $C_2F_5CF(OCH_3)CF(CF_3)_2$ with 1-bromopropane, trifluoromethyl benzene, hexamethyldisilazane, isobutyl acetate, methylisobutyl ketone, and trans-1,2-dichloroethylene using an ebulliometer or boiling point apparatus (Model MBP-100 obtained from Cal-Glass for Research, Inc, Costa Mesa, Calif.). An aliquot (25 to 30 milliliters (mL)) of the lower boiling component of the test compositions was added to the boiling point apparatus. The liquid was heated and allowed to equilibrate to its boiling point (typically about 30 minutes). After equilibration, the boiling point was recorded, an approximately 1.0 mL aliquot of the higher boiling component was added to the apparatus, and the resulting new composition was allowed to equilibrate for about 10 minutes, at which time the boiling point was recorded. The test continued basically as described above, with additions to the test mixture of about 1.0 mL of the higher boiling point component occurring every 10 minutes until 25 to 30 mL of the higher boiling point component had been added. This test procedure was repeated by starting with a 25–30 mL aliquot of the higher boiling component into the apparatus and adding approximately 1.0 mL aliquots of the lower boiling component. The presence of an azeotrope-like composition was noted when the test mixture exhibited a boiling point lower than the boiling point of the lower boiling point component.

The resulting azeotrope-like composition ranges are presented in Table 2. All boiling point determinations were run at standard pressure (760±1 torr).

TABLE 2

| Example | Organic Solvent | Organic Solvent Concentration (weight percent range) | $C_2F_5CF(OCH_3)CF(CF_3)_2$ Concentration (weight percent range) |
|---|---|---|---|
| 7 | 1-bromopropane | 19–99 | 1–81 |
| 8 | trifluoromethyl benzene | 1–77 | 23–99 |
| 9 | hexamethyldisilazane | 1–35 | 65–99 |
| 10 | isobutyl acetate | 1–32 | 68–99 |
| 11 | methylisobutyl ketone | 1–30 | 70–99 |
| 12 | trans-1,2-dichloroethylene | 41–99 | 1–59 |

In FIG. 1, line 11 is a plot of the boiling point versus the weight percent of $C_2F_5CF(OCH_3)CF(CF_3)_2$ in solution with 1-bromopropane. Horizontal line 12 indicates the boiling point of the lower boiling component. Points A and B, which show where line 11 and horizontal line 12 intersect, indicate the endpoints for the azeotrope-like composition.

Figure 2:
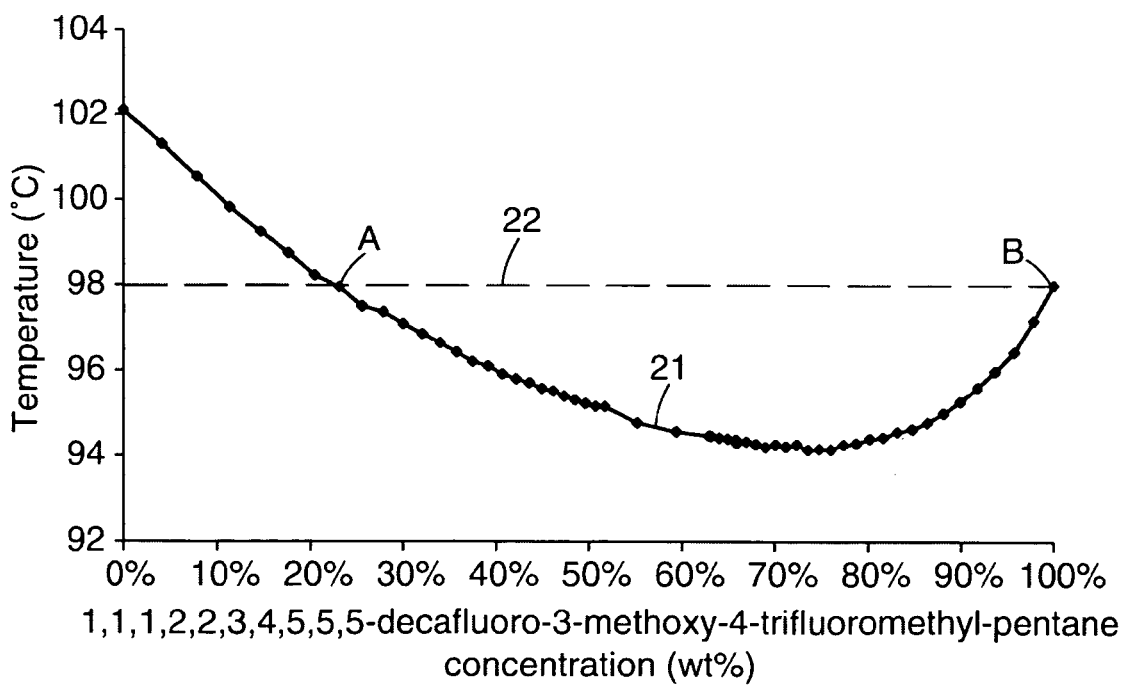
FIG. 2 is a graph of the boiling point versus the weight percent of $C_2F_5CF(OCH_3)CF(CF_3)_2$ in solution with trifluoromethylbenzene. Points A and B indicate the endpoints for the azeotrope-like composition.

In FIG. 2, line 21 is a plot of the boiling point versus the weight percent of $C_2F_5CF(OCH_3)CF(CF_3)_2$ in solution with trifluoromethylbenzene. Horizontal line 22 indicates the boiling point of the lower boiling component. Points A and B, which show where line 21 and horizontal line 22 intersect, indicate the endpoints for the azeotrope-like composition.

Figure 3:
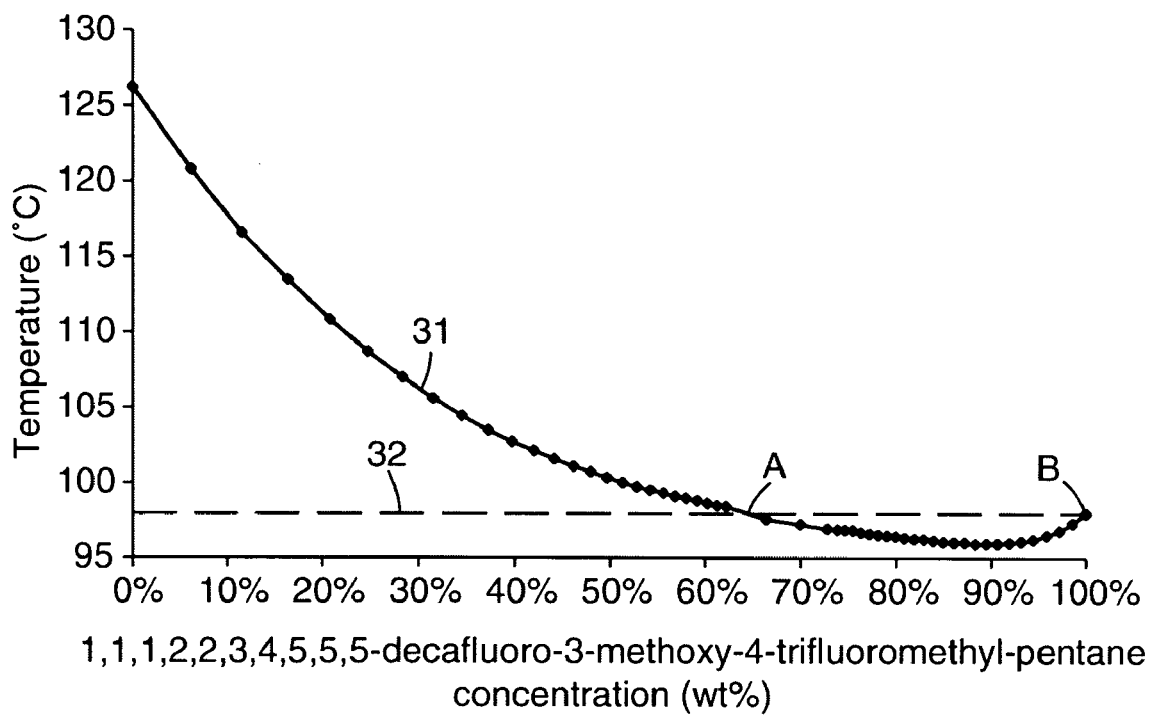
FIG. 3 is a graph of the boiling point versus the weight percent of $C_2F_5CF(OCH_3)CF(CF_3)_2$ in solution with hexamethyldisilazane. Points A and B indicate the endpoints for the azeotrope-like composition.

In FIG. 3, line 31 is a plot of the boiling point versus the weight percent of $C_2F_5CF(OCH_3)CF(CF_3)_2$ in solution with hexamethyldisilazane. Horizontal line 32 indicates the boiling point of the lower boiling component. Points A and B, which show where line 31 and horizontal line 32 intersect, indicate the endpoints for the azeotrope-like composition.

Figure 4:
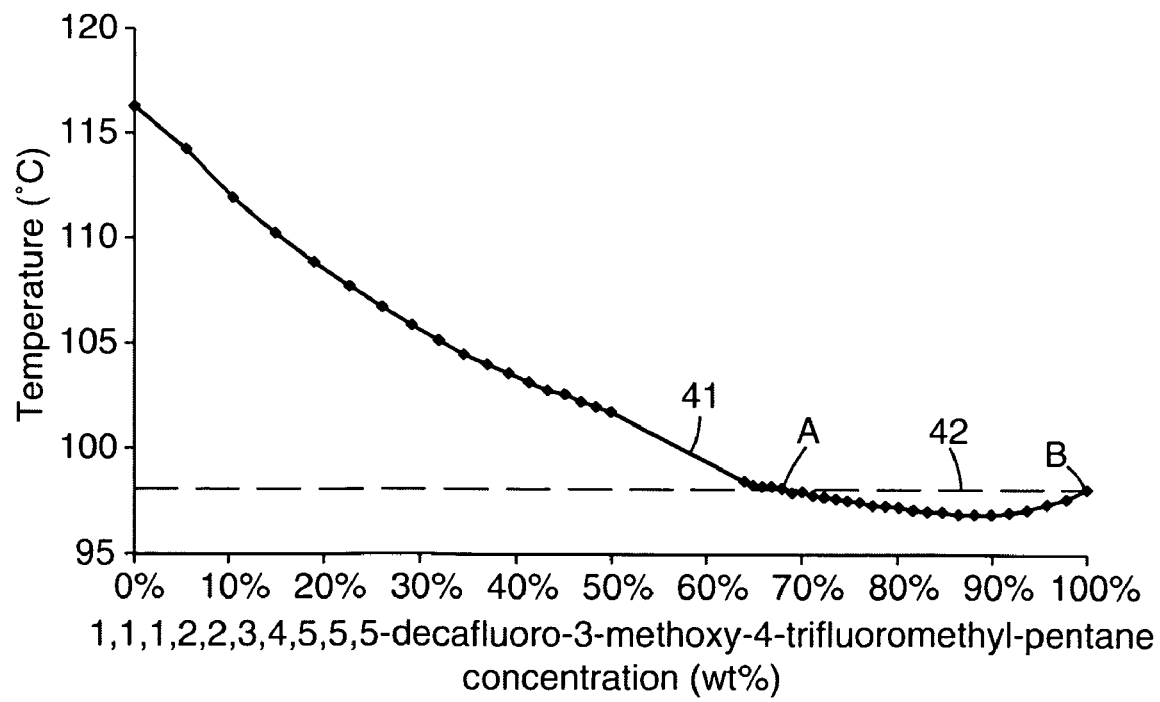
FIG. 4 is a graph of the boiling point versus the weight percent of $C_2F_5CF(OCH_3)CF(CF_3)_2$ in solution with isobutyl acetate. Points A and B indicate the endpoints for the azeotrope-like composition.

In FIG. 4, line 41 is a plot of the boiling point versus the weight percent of $C_2F_5CF(OCH_3)CF(CF_3)_2$ in solution with isobutyl acetate. Points A and B, which show where line 41 and horizontal line 42 intersect, indicate the endpoints for the azeotrope-like composition.

Figure 5:
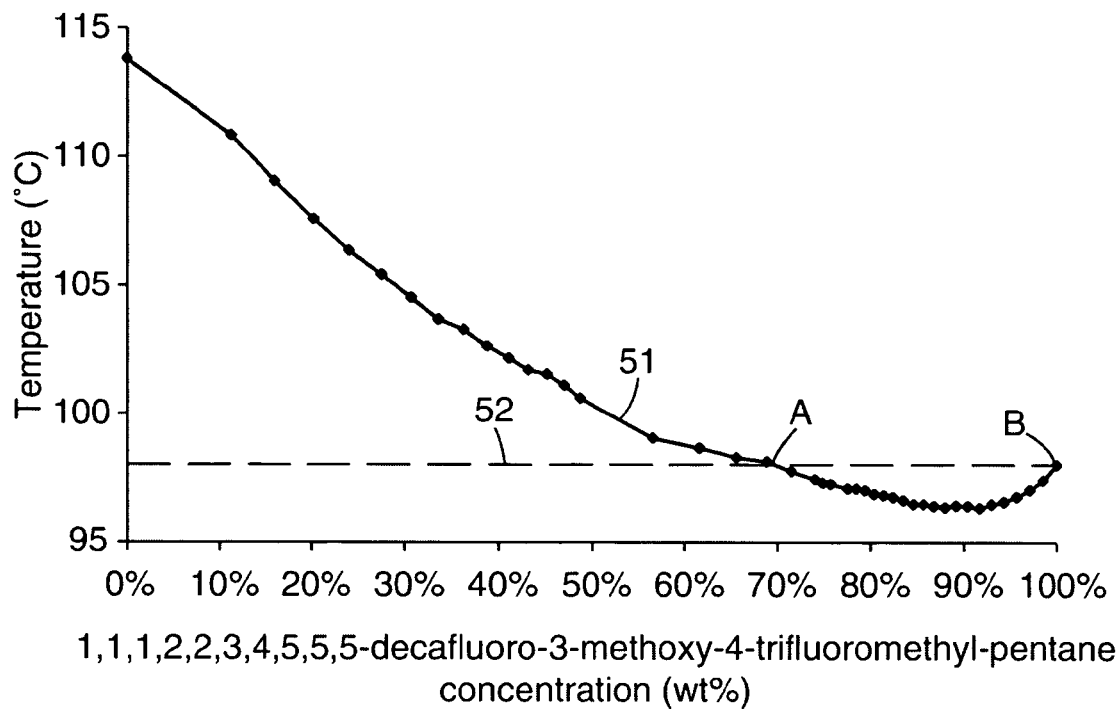
FIG. 5 is a graph of the boiling point versus the weight percent of $C_2F_5CF(OCH_3)CF(CF_3)_2$ in solution with methylisobutyl ketone. Points A and B indicate the endpoints for the azeotrope-like composition.

In FIG. 5, line 51 is a plot of the boiling point versus the weight percent of $C_2F_5CF(OCH_3)CF(CF_3)_2$ in solution with methylisobutyl ketone. Points A and B, which show where line 51 and horizontal line 52 intersect, indicate the endpoints for the azeotrope-like composition.

Figure 6:
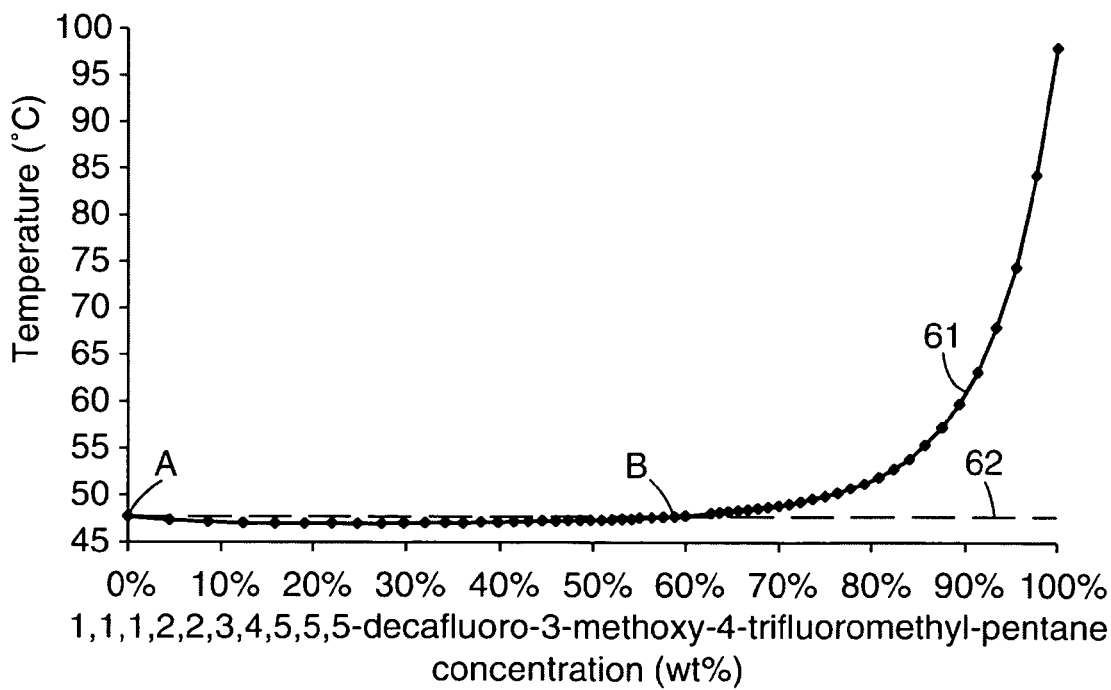
FIG. 6 is a graph of the boiling point versus the weight percent of $C_2F_5CF(OCH_3)CF(CF_3)_2$ in solution with trans-1,2-dichloroethylene. Points A and B indicate the endpoints for the azeotrope-like composition.

In FIG. 6, line 61 is a plot of the boiling point versus the weight percent of $C_2F_5CF(OCH_3)CF(CF_3)_2$ in solution with trans-1,2-dichloroethylene Points A and B, which show where line 61 and horizontal line 62 intersect, indicate the endpoints for the azeotrope-like composition.

Various modifications and alterations of this invention will become apparent to those skilled in the art without departing from the scope and spirit of this invention.

What is claimed is:

1. An azeotrope-like composition comprising a blend of
   (a) $C_2F_5CF(OCH_3)CF(CF_3)_2$; and
   (b) an organic solvent,
   wherein the blend is selected from the group consisting of
   (i) blends consisting essentially of about 1 to about 81 weight percent of $C_2F_5CF(OCH_3)CF(CF_3)_2$ and about 99 to about 19 weight percent of 1-bromopropane that boil below about 71.0° C. at about 101 kilopascals (kPa);
   (ii) blends consisting essentially of about 23 to about 99 weight percent of $C_2F_5CF(OCH_3)CF(CF_3)_2$ and about 77 to about 1 weight percent of trifluoromethylbenzene that boil below about 98.0° C. at about 101 kPa;
   (iii) blends consisting essentially of about 65 to about 99 weight percent of $C_2F_5CF(OCH_3)CF(CF_3)_2$ and about 35 to about 1 weight percent of hexamethyldisilazane that boil below about 97.9° C. at about 101 kPa;
   (iv) blends consisting essentially of about 68 to about 99 weight percent of $C_2F_5CF(OCH_3)CF(CF_3)_2$ and about 32 to about 1 weight percent of isobutyl acetate that boil below about 98.1° C. at about 101 kPa;
   (v) blends consisting essentially of about 70 to about 99 weight percent of $C_2F_5CF(OCH_3)CF(CF_3)_2$ and about 30 to about 1 weight percent of methylisobutyl ketone that boil below about 98.0° C. at about 101 kPa; and (vi) blends consisting essentially of about 1 to about 59 weight percent of $C_2F_5CF(OCH_3)CF(CF_3)_2$ and about 99 to about 41 weight percent of trans-1,2-dichloroethylene that boil below about 47.7° C. at about 101 kPa.

2. The azeotrope-like composition of claim 1, wherein the blend is selected from the group consisting of
   (i) blends consisting essentially of about 3 to about 78 weight percent of $C_2F_5CF(OCH_3)CF(CF_3)_2$ and about 97 to about 22 weight percent of 1-bromopropane that boil below about 70.0° C. at about 101 kPa;
   (ii) blends consisting essentially of about 30 to about 97 weight percent of $C_2F_5CF(OCH_3)CF(CF_3)_2$ and about 70 to about 3 weight percent of trifluoromethylbenzene that boil below about 97.0° C. at about 101 kPa;
   (iii) blends consisting essentially of about 68 to about 99 weight percent of $C_2F_5CF(OCH_3)CF(CF_3)_2$ and about 32 to about 1 weight percent of hexamethyldisilazane that boil below about 97.4° C. at about 101 kPa;
   (iv) blends consisting essentially of about 71 to about 99 weight percent of $C_2F_5CF(OCH_3)CF(CF_3)_2$ and about 29 to about 1 weight percent of isobutyl acetate that boil below about 97.8° C. at about 101 kPa;
   (v) blends consisting essentially of about 73 to about 99 weight percent of $C_2F_5CF(OCH_3)CF(CF_3)_2$ and about 27 to about 1 weight percent of methylisobutyl ketone that boil below about 97.6° C. at about 101 kPa; and
   (vi) blends consisting essentially of about 2 to about 55 weight percent of $C_2F_5CF(OCH_3)CF(CF_3)_2$ and about 98 to about 45 weight percent of trans-1,2-dichloroethylene that boil below about 47.6° C. at about 101 kPa.

3. The azeotrope-like composition of claim 1, wherein the blend is selected from the group consisting of
   (i) blends consisting essentially of about 7 to about 74 weight percent of $C_2F_5CF(OCH_3)CF(CF_3)_2$ and about 93 to about 26 weight percent of 1-bromopropane that boil below about 68.9° C. at about 101 kPa;
   (ii) blends consisting essentially of about 39 to about 94 weight percent of $C_2F_5CF(OCH_3)CF(CF_3)_2$ and about 61 to about 6 weight percent of trifluoromethylbenzene that boil below about 96.1° C. at about 101 kPa;
   (iii) blends consisting essentially of about 73 to about 98 weight percent of $C_2F_5CF(OCH_3)CF(CF_3)_2$ and about 27 to about 2 weight percent of hexamethyldisilazane that boil below about 96.9° C. at about 101 kPa;
   (iv) blends consisting essentially of about 76 to about 97 weight percent of $C_2F_5CF(OCH_3)CF(CF_3)_2$ and about 24 to about 3 weight percent of isobutyl acetate that boil below about 97.5° C. at about 101 kPa;
   (v) blends consisting essentially of about 77 to about 98 weight percent of $C_2F_5CF(OCH_3)CF(CF_3)_2$ and about 23 to about 2 weight percent of methylisobutyl ketone that boil below about 97.2° C. at about 101 kPa; and
   (vi) blends consisting essentially of about 5 to about 50 weight percent of $C_2F_5CF(OCH_3)CF(CF_3)_2$ and about 95 to about 50 weight percent of trans-1,2-dichloroethylene that boil below about 47.4° C. at about 101 kPa.

4. The azeotrope-like composition of claim 1, wherein the composition is an azeotrope and the blend is selected from the group consisting of
   (i) blends consisting essentially of about 55.4 weight percent of $C_2F_5CF(OCH_3)CF(CF_3)_2$ and about 44.6 weight percent of 1-bromopropane that boil at about 65.4° C. at about 97.8 kPa;
   (ii) blends consisting essentially of about 71.3 weight percent of $C_2F_5CF(OCH_3)CF(CF_3)_2$ and about 28.7 weight percent of trifluoromethylbenzene that boil at about 92.3° C. at about 97.7 kPa;
   (iii) blends consisting essentially of about 90.0 weight percent of $C_2F_5CF(OCH_3)CF(CF_3)_2$ and about 10.0 weight percent of hexamethyldisilazane that boil at about 93.6° C. at about 97.3 kPa;
   (iv) blends consisting essentially of about 91.8 weight percent of $C_2F_5CF(OCH_3)CF(CF_3)_2$ and about 8.2 weight percent of isobutyl acetate that boil at about 94.5° C. at about 96.8 kPa;
   (v) blends consisting essentially of about 90.5 weight percent of $C_2F_5CF(OCH_3)CF(CF_3)_2$ and about 9.5 weight percent of methylisobutyl ketone that boil at about 94.0° C. at about 96.6 kPa; and
   (vi) blends consisting essentially of about 22.7 weight percent of $C_2F_5CF(OCH_3)CF(CF_3)_2$ and about 77.3 weight percent of trans-1,2-dichloroethylene that boil at about 45.7° C. at about 98.6 kPa.

5. A coating composition comprising an azeotrope-like composition according to claim 1 and at least one coating material.

6. A coated article comprising a substrate having a first surface, wherein the coating composition of claim 5 contacts at least a portion of the first surface.

7. A process for depositing a coating on a substrate surface comprising the step of applying the coating composition of claim 5 to at least a portion of at least one surface of the substrate, wherein the at least one coating material is soluble or dispersible in the azeotrope-like composition.

8. A working fluid comprising the azeotrope-like composition according to claim 1 and a lubricious additive.

9. The working fluid according to claim 8, wherein said lubricious additive is volatile.

10. The azeotrope-like composition of claim 1, further comprising ozone.

11. The azeotrope-like composition of claim 1, further comprising hydrofluoric acid.

12. A process for metal, cermet, or composite working fluid wherein said process is lubricated using the working fluid of claim 8.

13. A process for removing contaminants from the surface of a substrate comprising the steps of contacting the substrate with one or more of the azeotrope-like compositions according to claim 1 until the contaminants are dissolved, dispersed, or displaced in or by the azeotrope-like composition, and removing the azeotrope-like composition containing the dissolved, dispersed or displaced contaminants from the surface of the substrate.

14. A process for heat transfer wherein one or more of the azeotrope-like compositions according to claim 1 is used as a heat-transfer fluid.

* * * * *